US00PP21522P3

(12) United States Plant Patent
Ponto

(10) Patent No.: US PP21,522 P3
(45) Date of Patent: Nov. 23, 2010

(54) ***AGAPANTHUS* PLANT NAME 'PONTO'S QUEEN OF THE NILE'**

(50) Latin Name: *Agapanthus africanus*
Varietal Denomination: Ponto's Queen of the Nile

(75) Inventor: William H. Ponto, Vista, CA (US)

(73) Assignee: Ponto Nursery, Inc., Vista, CA (US)

( * ) Notice: Subject to any disclaimer, the term of this patent is extended or adjusted under 35 U.S.C. 154(b) by 0 days.

(21) Appl. No.: 12/315,941

(22) Filed: Dec. 9, 2008

(65) Prior Publication Data

US 2010/0146677 P1 Jun. 10, 2010

(51) Int. Cl.
*A01H 5/00* (2006.01)

(52) U.S. Cl. ..... Plt./398

(58) Field of Classification Search ..... Plt./263, Plt./398
See application file for complete search history.

(56) References Cited

U.S. PATENT DOCUMENTS

PP10,866 P * 4/1999 Mendoza ..... Plt./398

* cited by examiner

*Primary Examiner*—Susan B McCormick Ewoldt
(74) *Attorney, Agent, or Firm*—The Maxham Firm

(57) ABSTRACT

A new and distinct selection of *Agapanthus africanus* (commonly known as Lily of the Nile) which herein is referred to as *Agapanthus africanus* cv. 'Ponto's Queen of the Nile.' 'Ponto's Queen of the Nile' differs from its parent plant, *Agapanthus africanus* Queen Ann, by possessing a gold leaf with a dark green stripe in the middle rather than an all-green leaf. The flower stock is green with a gold stripe as well.

4 Drawing Sheets

Latin name of the genus and species of the plant claimed: *Agapanthus* Plant named: 'Ponto's Queen of the Nile'.

Latin name: *Agapanthus africanus.*

Variety denomination: 'Ponto's Queen of the Nile'.

BACKGROUND OF THE INVENTION

This invention relates to a new and distinct selection of *Agapanthus africanus* Queen Ann, a member of the Alliancae family. *Agapanthus* is commonly known as Lily of the Nile. *Agapanthus africanus* cv. 'Ponto's Queen of the Nile,' this new variety, originated as a selected seedling from *Agapanthus africanus* Queen Ann, a self pollinating, non patent plant. The discovery was made in Vista, Calif., in 1998. The plant to date is known to exist only within the boundaries of the location of the discovery, and has not been described in any publication. This distinctive plant was selected out, allowed to develop and mature, and then asexually reproduced by divisions. Each of the progeny exhibit identical characteristics to the original selected prototype, establishing this variety as stable and true to type when produced by asexual means.

This new cultivar has been strictly asexually reproduced by divisions only within the boundaries of this location at the nursery of origin. Sexual reproduction such as seed propagation would not produce a true form of this cultivar and would result in loss of selected attributes. The divisions have been asexually reproduced for the last ten years, thereby establishing this cultivar as a new and distinctive plant. This plant is unknown in any written publication found.

BRIEF SUMMARY OF THE INVENTION

The new variety is consistent with its parent plant, *Agapanthus africanus* Queen Ann in regard to hardiness. It appears to be hardy to 29° F. The flower is typical of the parent plant, blooming in late spring and early summer. The flower longevity is one to three weeks.

This new variety, *Agapanthus africanus* cv. 'Ponto's Queen of the Nile,' differs from its' parent plant, *Agapanthus africanus* Queen Ann, by a characteristic gold leaf with a dark green stripe in the middle, rather than an all-green leaf. The flower stock, or peduncle, is green with a gold stripe as well.

This new variety would make an excellent border for a lawn. It can also be used in flower beds as well as a container plant for the patio. This plant is suitable for use as an annual when temperatures dip below 29° F. and a perennial in all other areas.

There were no known pathogens or insects observed that were not typical of any *Agapanthus africanus.*

BRIEF DESCRIPTION OF THE DRAWING

The accompanying photographs show a typical specimen of the plant according to this invention in full color, demonstrating the unique and distinctive coloration of the leaves and flower stock or peduncle, the color rendition being as nearly true as it is possible to obtain by conventional procedures, in which.

DETAILED BOTANICAL DESCRIPTION

The following is a detailed description of the new *Agapanthus africanus* cv. 'Ponto's Queen of the Nile,' the color terminology being from the Pantone color chart.

Figure 1:
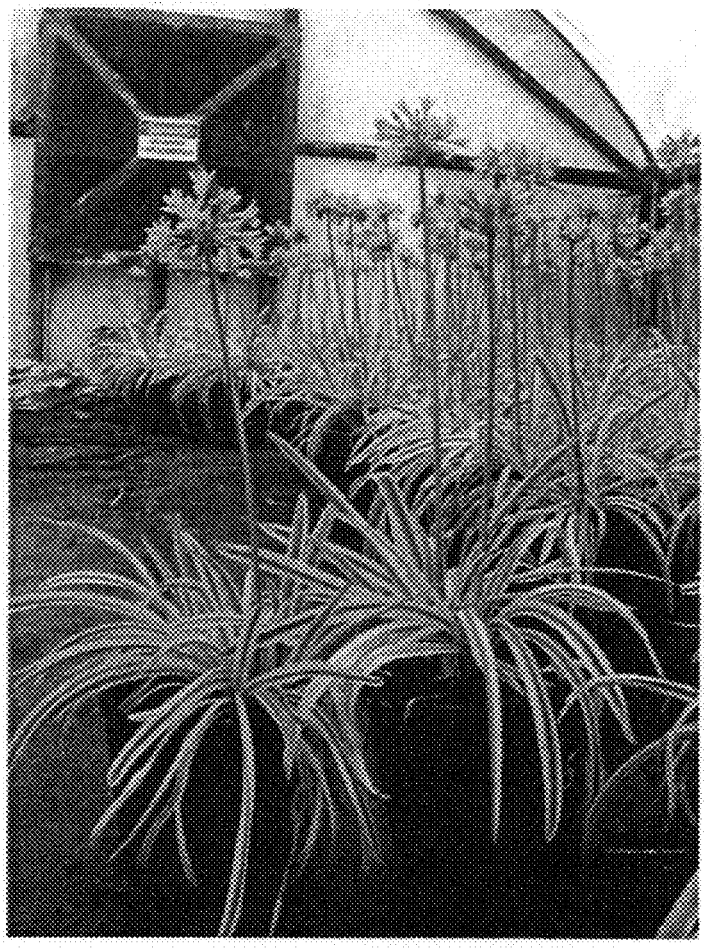
FIG. 1 shows the complete plant of the new variety in two five-gallon containers at 4 years of age.
Figure 4:
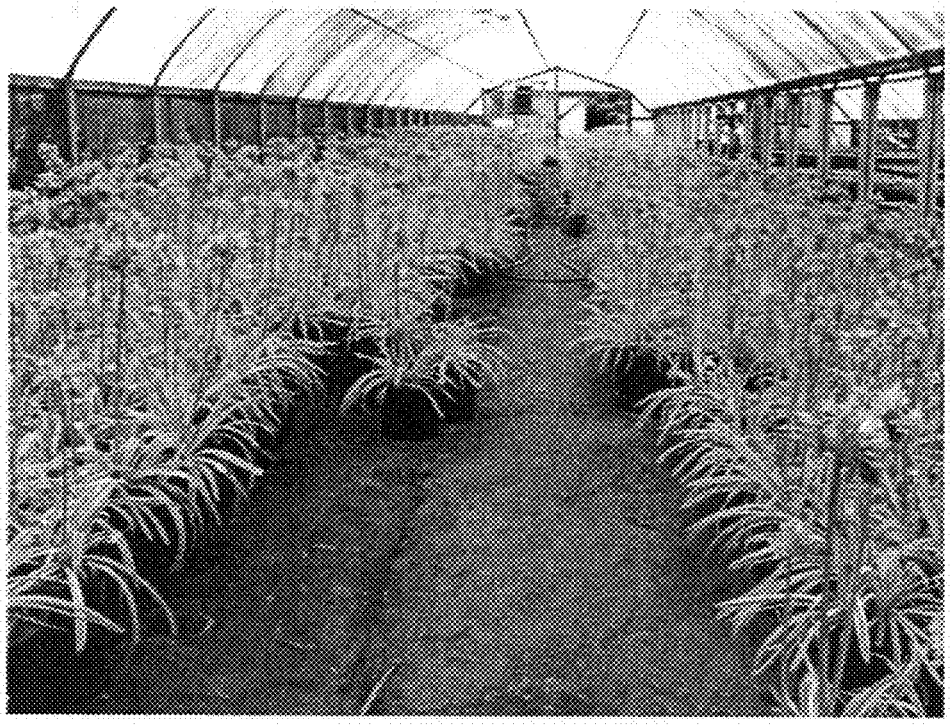
FIG. 4 shows a greenhouse full of the new variety in a multiplicity of five-gallon containers.
Figure 5:
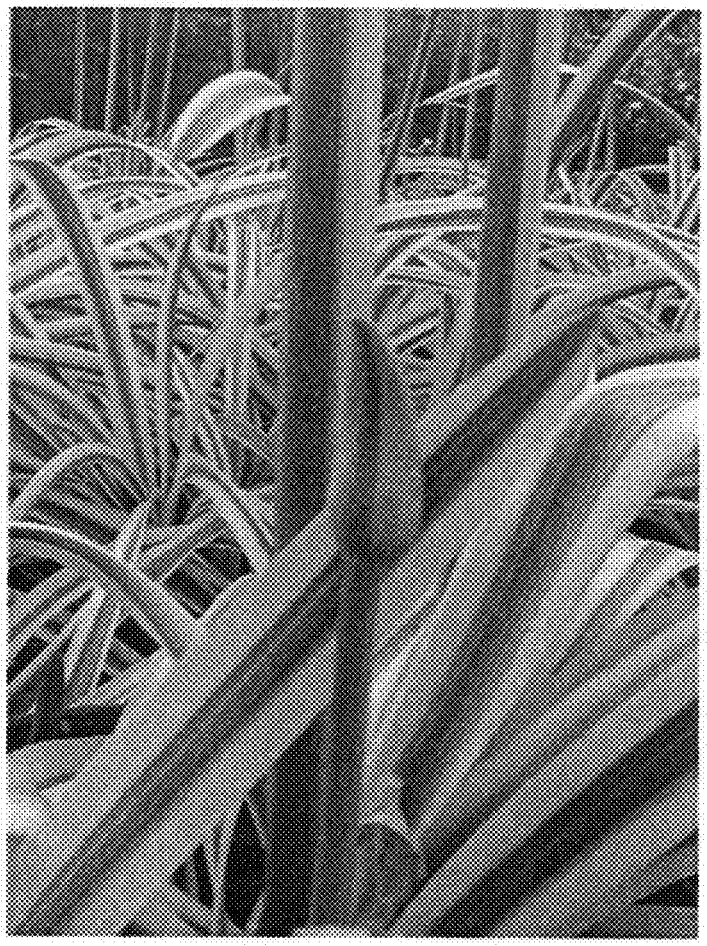
FIG. 5 is a close-up view of leaves and a peduncle showing the striping of this new variety.
Figure 7:
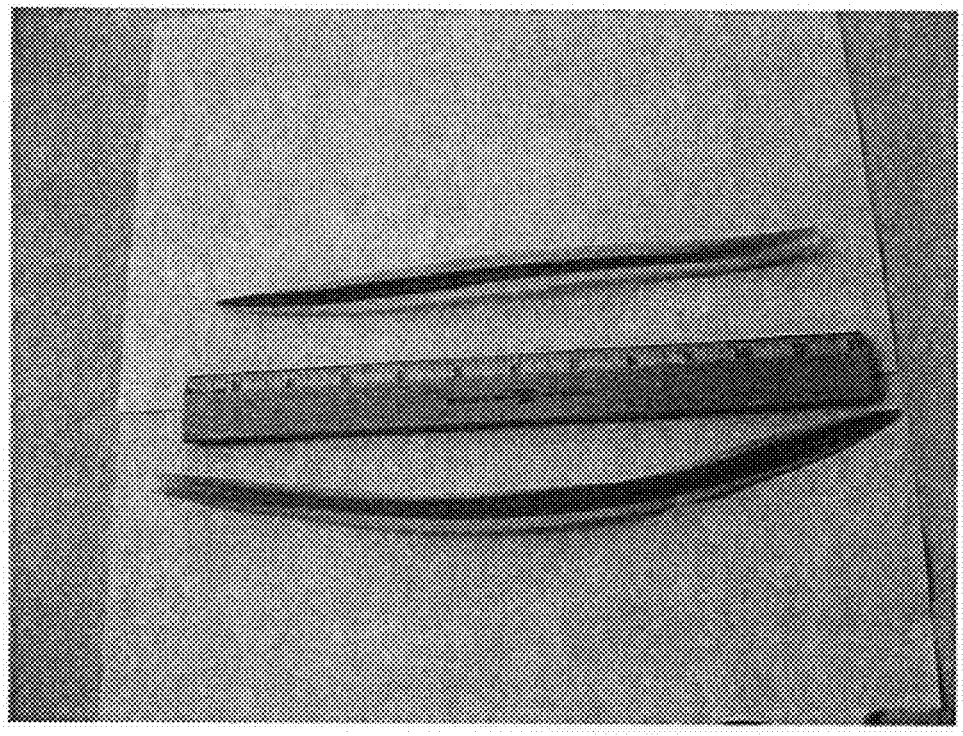
FIG. 7 shows two leaves of this new variety in relation to a ruler.

Foliage: *Agapanthus africanus* cv. 'Ponta's Queen of the Nile' has the same general growth habit of the parent plant *Agapanthus africanus* cv. Queen Ann. Where the known cultivars have leaves that are all green, the leaves of this invention are yellow and green, as described in detail herein. The leaves are elongated, eleven to thirteen inches (27.9 to 33.02 cm) in length (FIG. 7), with the apex being pointed, the base being broad at about one inch (2.5 cm) across. There is no visible venation pattern or color in the leaves. The leaves grow upward and then cascade to a mound of twenty six to thirty one inches (66.04 to 76.20 cm) across, resulting in the plant's habit of being upright and cascading, as shown in FIGS. 1 and 4. There are about eight to 14 leaves, the number increasing as the plant matures. The plant produces pubs from its roots. The leaf of the new *Agapanthus africanus* cv. 'Ponto's Queen of the Nile' is about one inch (2.5 cm) wide for most of its length and has linear borders of one quarter inch (0.635 cm) wide of yellow color 101-C tapering to the apex, as shown in FIGS. 5 and 7. The linear center of the leaf has a green stripe of color 574-C one half inch (1.27 cm) in width, tapering to the apex. The striping continues through the entire length of the leaf and is the same on both top and bottom sides. The leaf texture is smooth, both top and bottom.

Figure 2:
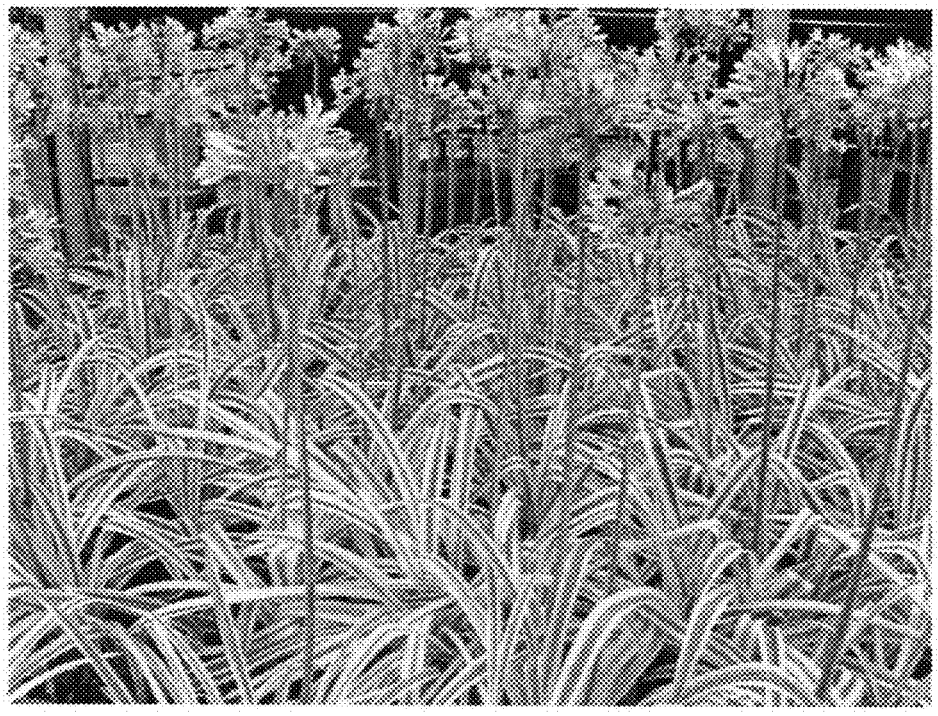
FIG. 2 shows many of the plants of this new variety, revealing the uniformity of the foliage.
Figure 3:
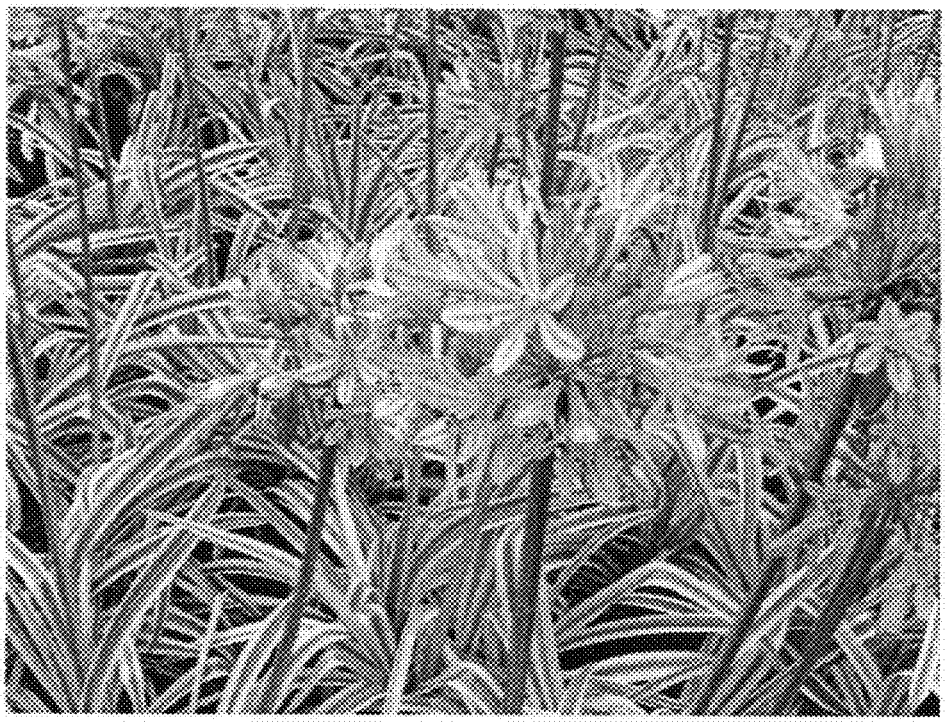
FIG. 3 shows the color of the inflorescence and its relationship to the foliage.
Figure 6:
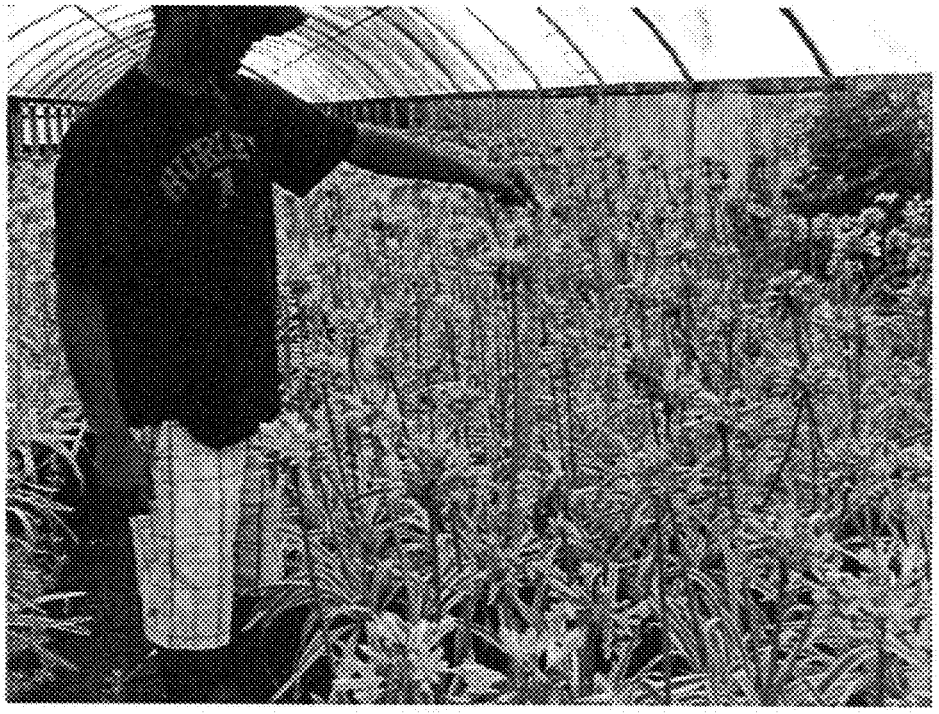
FIG. 6 shows the height of a stock of this new variety in relation to a yardstick.

Inflorescence: The flowers, having no significant fragrance, are produced at the end of a peduncle of twenty three to thirty one inches (58.42 to 78.74 cm) in length (FIGS. 1, 2, and 6). The peduncle is green in color 574-C with a yellow stripe of color 101-C and has a smooth texture. See FIGS. 1, 2, 3, and 5. The blooms are an umbel flower cluster about 4 to 4½ inches (10 to 11.25 cm) across with fifty to seventy five tubular flowers, as shown in FIGS. 2 and 3. Each flower has six petals in a spread arrangement, about 2½ to 3 inches (6.25 to 7.5 cm) across and about one inch (2.5 cm) in height from its base. The flowers are lavender blue in color 2708-C with a darker lavender stripe through each petal of color 2716-C. See FIGS. 1-3. The petals are about 1½ (3.75 cm) long and about ¼ inch (0.635 cm) wide, having an elongated, somewhat almond shape. The flower buds are generally round, approximately one inch in diameter. The flower produces seeds that are a narrow oval, about ⅛ inch (0.3 cm) long, 1/16 (0.15 cm) wide, and black in color. The seeds are fertile and do germinate but they do not produce a plant true to cultivar.

What is claimed is:

1. A new and distinctive *Agapanthus africanus* plant as herein described and illustrated, that is characterized by a yellow gold leaf with a green stripe through the middle, and a green peduncle with a yellow linear stripe.

* * * * *